United States Patent [19]
Okudaira et al.

[11] Patent Number: 5,962,511
[45] Date of Patent: *Oct. 5, 1999

[54] DRUGS FOR ALLERGIC AND EOSINOPHILIC DISEASES

[75] Inventors: Hirokazu Okudaira; Akio Mori, both of Tokyo, Japan

[73] Assignee: Environmental Research Institute, Inc., Tokyo, Japan

[*] Notice: This patent is subject to a terminal disclaimer.

[21] Appl. No.: 09/102,088

[22] Filed: Jun. 22, 1998

Related U.S. Application Data

[62] Division of application No. 08/841,683, Apr. 30, 1997, abandoned.

[30] Foreign Application Priority Data

Mar. 8, 1995 [JP] Japan ................................ 7-77429
Apr. 3, 1995 [JP] Japan ................................ 7-101696

[51] Int. Cl.⁶ ............................................. A01N 43/02
[52] U.S. Cl. ....................................... 514/450; 514/485
[58] Field of Search .................................... 514/450, 485

[56] References Cited

U.S. PATENT DOCUMENTS 4,843,092  6/1989  Shichi et al. ........................ 514/450
5,721,270  2/1998  Okudaira et al. .................... 514/450

OTHER PUBLICATIONS

Callewaert et al., "Tetranactin, a Macrotetrolide Antibiotic, Suppresses in vitro Proliferation of Human Lymphocytes and Generation of Cytotoxicity", *Immunopharm.* 16:25–32 (1988).

Egan et al., "Inhibition of Pulmonary Eosinophilia and Hyperactivity by Antibodies to Interleukin–5", *International Archives Allergy and Immunology* 107:321–322 (1995).

Lopez et al., "Recombinant Human Interleukin 5 is a Selective Activator of Human Eosinophil Function", *Journal of Experimental Medicine* 167:219–224 (Jan. 1988).

Mori et al., "Atopic Diseases and Eosinophilic Inflammation–Possible Management with Agents Which Downregulate IL–5 Gene Transcription", *Environmental Dermatology* 1(1):42–54 (Apr. 1994).

Mori et al., "Regulation of Interleukin–5 Production by Peripheral Blood Mononuclear Cells from Atopic Patients with FK506, Cyclosporin A and Glucocorticoid", *International Archives Allergy and Immunology* 104(Supp. 1):32–35 (1994).

Mori et al., "Allergen–Specific Human T Cell Clones Produce Interleukin–5 upon Stimulation with the Th1 Cytokine Interleukin–2", *International Archives of Allergy and.*

Mori et al., "IL–5 Production by CD4+ T Cells of Asthmatic Patients is Suppressed by Glucocorticoids and the Immunosuppressants FK506 and Cyclosporin A", *international Immunology* 7(3):449–457 (1995).

Okudaira et al., "Enhanced Production and Gene Expression of IL–5 in Bronchial Asthma", *Allergy and Clinical Immunology News* 6/1:19–25 (1994).

Tanouchi et al., "Immunosuppressive Effects of Polynactins (Tetranactin, Trinactin and Dinactin) on Experimental Autoimmune Uveoretintis in Rats", *Jpn. J. Ophthalmol.* 31:218–229 (1987).

Sheffer, "International Consensus Report on the Diagnosisi and Management of Asthma", *Clinical and Experimental Allergy Report* 22(Supp. 1):1–72 (May 1992).

Tanouchi et al., "Immunosuppressive and Anti–Proliferative Effects of a Macrotetroide Antibiotic, Tetranactin", *Immunology* 63:471–475 (1988).

*Primary Examiner*—Frederick Krass
*Attorney, Agent, or Firm*—Pillsbury Madison & Sutro LLP

[57] ABSTRACT

A method of inhibiting human IL-5 gene transcriptions mRNA expression and protein production by human T-cells using one or more compounds selected from those shown by formula I shown below (where $R_1$, $R_2$, $R_3$ and $R_4$ are each independently a $C_1$–$C_6$ alkyl group) and a therapeutic agent for allergic and eosinophilic inflammatory diseases which contains one or more compounds selected from those shown by the formula.

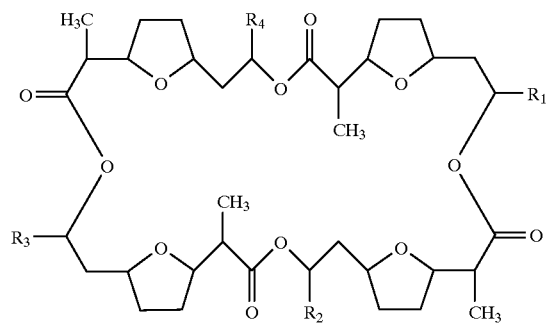

4 Claims, 10 Drawing Sheets

*Fig. 10B* ns and human IL-5 gene transcription and mRNA expression using macrolide antibiotics shown by formula 1, as well as therapeutic agents containing the above-mentioned substances for allergic and eosinophilic diseases.

DRUGS FOR ALLERGIC AND EOSINOPHILIC DISEASES

This is a division of application Ser. No. 08/841,683, filed Apr. 30, 1997, now abandoned.

TECHNICAL SCOPE

This invention related to a method of inhibiting the production of human IL-5 by human T-cells and human IL-5 gene transcription and mRNA expression using macrolide antibiotics shown by formula 1, as well as therapeutic agents containing the above-mentioned substances for allergic and eosinophilic diseases.

BACKGROUND TECHNOLOGIES

Type-I (based on classification of Coombs and Gell) allergic diseases, such as bronchial asthma, atopic dermatitis and allergic rhinitis, have been understood to be mainly caused by IgE-mediated release of chemical mediators from mast cells and basophils.

Recent immunological studies have shown, however, that tissue-damaging chronic inflammatory reactions, mainly by T-cells and eosinophils, are closely related to various allergic diseases. The International Asthma Committee report announced in 1992 no longer describes bronchial asthma as simple immediate-type hypersensitivity, but a chronic inflammatory disease due mainly to T-cells and eosinophils. This naturally has led clinicians to attach greater importance to the control of chronic inflammation, which underlies airway obstruction, in its treatment. Anti-inflammatory therapy, mainly using steroids, is recommended as therapy of first choice.

Infiltration of eosinophils into tissues is a common feature of allergic diseases such as bronchial asthma and atopic dermatitis, as well as so-called eosinophilic diseases. Eosinophil granule-derived basic proteins such as major basic protein (MBP), eosinophil cationic protein (ECP) and eosinophil-derived peroxidase (EPO) have great tissue-damaging effects, causing tissue destruction and marked inflammatory reactions. Eosinophils serve as effector cells in inflammatory reactions. As mentioned above, recent studies have shown that the cytokine IL-5 produced by activated T-cells play an important role in eosinophils' infiltration into tissues and activation [(H. Okudaira et al, Allergy and Clinical Immunology News, 6/1, 19–25 (1994); A. Mori et al, International Archives Allergy and Immunology 104, 32–35 (1994)]. IL-5 is a cytokine with a molecular weight of about 13 KDa and is mainly produced by activated T-cells. In humans, it has been shown to specifically affect eosinophils and enhance their growth, differentiation and cytotoxicity (effector function), as well as to enhance the release of mediators (such as leukotriene, MBP, etc.) by them (Lopez A. F. et al, Journal of Experimental Medicine, 167: 219–224, 1988). Many investigators have shown in animal models that neutralization of IL-5 results in marked inhibition of bronchial asthma reactions and infiltration of cells such as eosinophils (Egan R. W., 15th International Allergic Society Meeting Report and the 20th CIA Meeting Report).

The inventors have conducted immunological studies on the pathology of bronchial asthma and found that IL-5 production by CD4-positive T-cells in peripheral blood is significantly greater in both atopic and non-atopic bronchial asthma patients than in healthy volunteers. A close correlation was found between therapeutic efficacy and IL-5 production in asthma patients (A. Mori, et al., International Immunology 7: 449–457, 1995). The inventors showed in vitro experiments that steroids, FK506 (an immunosuppressive agent) and cyclosporine A dose-dependently inhibit the production of IL-5 by T-cells (A. Mori, et al, International Immunology 7: 449–457, 1995). In the clinical experience of the inventors, symptomatic bronchial asthma patients show marked improvement in clinical symptoms and laboratory tests within 1 week after treatment with steroids (inhalation). These improvements are associated with decreases in blood eosinophil counts and reduced production of IL-5 by peripheral CD4-positive T-cells. Furthermore, symptoms such as skin eruption and itching drastically improve within several days after local administration of FK506 in very severe atopic dermatitis patients. Production of IL-5 by peripheral CD4-positive T-cells is also markedly inhibited in these patients. The inventors therefore thought that IL-5 production inhibitors should be useful for treating allergic diseases associated with eosinophilic inflammation.

Screening of drugs for ability to inhibit IL-5 is expected to be useful for efficiently discovering those which are clinically effective for allergic and eosinophilic diseases [(A. Mori, et al, Environmental Dermatology, 1, 42–54 (1994); A. Mori, et al, International Archives of Allergy and Immunology, 104, 32–35 (1994)]. The inventors have demonstrated the importance of IL-5 production by T-cells in the onset of allergic diseases in both basic and clinical medical studies. In the belief that inhibition of IL-5 production by T-cells would be very effective for controlling eosinophilic inflammation, we investigated various immunosuppressive agents both in vitro and in vivo. Steroids, which strongly inhibit IL-5 production in vitro, have long been used as the only drugs with remarkable efficacy for severe bronchial asthma and atopic dermatitis, but they cause various serious adverse reactions such as diabetes, hypertension and cataracts. As a result, the development of non-steroidal IL-5 inhibitors which inhibit eosinophilic inflammation by inhibiting IL-5 production like steroids but are devoid of adverse reactions has been desired.

As a result of various studies to achieve this objective, the inventors discovered that macrolide antibiotics produced by actinomycetes (shown by formula 1) markedly inhibit the production of IL-5 by human T-cells.

BRIEF EXPLANATION OF THE DRAWINGS

1. Unstimulated
2. Concanavalin A 10 μg/ml
3. 2+nonactin 1 nM
4. 2+nonactin 10 nM
5. 2+nonactin 100 nM
6. 2+nonactin 1 μM

1. Unstimulated
2. Stimulated by anti-CD3 antibody
3. 2+nonactin 1 nM
4. 2+nonactin 10 nM
5. 2+nonactin 100 nM
6. 2+nonactin 1μM

1. Unstimulated
2. Concanavalin A 10 μg/ml
3. 2+nonactin 1 μM
4. 2+nonactin 100 nM
5. 2+nonactin 10 nM

1. Unstimulated
2. PMA 20 nM+IOM 1 μM
3. 2+nonactin 100 nM

FIG. 5(a) shows the effects of nonactin on IL-2 and FIG. 5(b) IL-4 production. The numbers in this figure indicate the following:

1. Unstimulated
2. Concanavalin A 10 μg/ml
3. 2+nonactin 1 nM
4. 2+nonactin 100 nM
5. 2+nonactin 10 nM

1. Unstimulated
2. PMA+IOM
3. 2+nonactin 1 μM
4. 2+nonactin 100 nM
5. 2+nonactin 10 nM

1. Unstimulated
2. PMA+IOM
3. 2+nonactin 100 nM

1. Unstimulated
2. PMA+IOM
3. 2+nonactin 100 nM

1. No antigen
2. Vehicle
3. Nonactin

DETAILED EXPLANATION OF THE INVENTION

The present invention offers a method of inhibiting human IL-5 gene transcription, mRNA expression and protein production by human T-cells using one or two or more compounds selected from those represented by formula I shown below (where $R_1$, $R_2$, $R_3$ and $R_4$ are each independently a $C_1$–$C_6$ alkyl group).

The present invention makes it possible to specifically inhibit IL-5 without inhibiting IL-2 or IL-4 gene transcription or production.

The present invention also offers therapeutic agents for allergic diseases or eosinophilic inflammatory diseases which contain 1 or 2 or more compounds selected from those represented by formula I shown below (where $R_1$, $R_2$, $R_3$ and $R_4$ are each independently a $C_1$–$C_6$ alkyl group).

Allergic diseases which can be treated by therapeutic agents covered by the present invention include bronchial asthma, atopic dermatitis, pollinosis, allergic rhinitis and allergic conjunctivitis.

Eosinophilic inflammatory diseases (hereafter referred to as eosinophilic diseases) which can be treated by therapeutic agents covered by the present invention include eosinophilic syndrome, allergic angiitis, eosinophilic fasciitis, eosinophilic pneumonia, PIE syndrome and other diseases associated with eosinophilia.

More details on the present invention are given below according to the desirable mode.

In order to conduct studies on IL-S production by human T-cells, the inventors established allergen-specific T-cell clones from peripheral mononuclear cells from allergic patients, used these T-cell clones to establish T-cell hybridomas and screened drugs that inhibit IL-5 production using these T-cell lines and peripheral lymphocytes from atopic patients with a marked ability to produce IL-5.

As a result, they found that compounds with the chemical formulae shown by formula I inhibit human IL-5 production by human T-cells.

In formula I, $R_1$, $R_2$, $R_3$ and $R_4$ are each independently a $C_1$–$C_6$ alkyl group. They may either be the same or different, but preferably, $R_1$, $R_2$, $R_3$ and $R_4$ should be methyl or ethyl groups. The most desirable compounds are nonactin, monactin, dinactin, trinactin and tetranactin, which have the following structures:

Nonactin: $R_1=R_2=R_3=R_4=-CH_3$
Monactin: $R_1=R_2=R_3=-CH_3$; $R_4=-C_2H_5$
Dinactin: $R_1=R_2=-CH_3$; $R_3=R_4=-C_2H_5$
Trinactin: $R_1=-CH_3$; $R_2=R_3=R_4=-C_2H_5$
Tetranactin: $R_1=R_2=R_3=R_4=-C_2H_5$ The methods and therapeutic agents of the present invention use 1 or 2 or more compounds selected from those represented by formula I above alone or in combination. The most desirable compound is nonactin. Monactin, dinactin, trinactin and tetranactin, derivatives of nonactin with modified side chains, have the same basic structure and similar effects as nonactin (U.S. Pat. No. 4,843,092, Jun. 27, 1989) and can be used in the same manner as nonactin for the purpose of the present invention.

The currently known T-cell-specific immunosuppressive agents Cyclosporine and FK506 are both macrolide antibiotics produced by actinomycetes. Nonactin, monactin, dinactin, trinactin and tetranactin used in the method and therapeutic agents in the present invention are also produced by actinomycetes. Tetranactin was shown to inhibit the growth of T-cells and induction of NK cells (Tanouchi et al, Immunopharmacology, 16, 25–32, 1988). It was also found to inhibit antibody production and exert therapeutic efficacy against experimental autoimmune uveitis in rats (Tanouchi et al, Jpn. J. Ophthalmol., 31, 218–229, 1987; Shichi et al, U.S. Pat. No. 4,843,092, Jun. 27, 1989; Tanouchi et al, Immunology, 63, 471–475, 1988). On the basis of these findings, nonactin and its related compounds are expected to be useful for controlling rejection after organ transplantation, as well as for treating autoimmune diseases such as rheumatoid arthritis, systemic lupus erythematosus, glomerulonephritis, uveitis and thyroid autoimmune disease, and a patent was accordingly filed (Shichi et al, U.S. Pat. No. 4,843,092, Jun. 27, 1989). However, this patent neither indicates nor recommends their use as drugs for allergic or eosinophilic diseases.

Prior to the accomplishment of the present invention, nobody had shown that nonactin, monactin, dinactin, trinactin or tetranactin inhibit IL-5 gene transcription, mRNA expression or protein production by human T-cells. Furthermore, no one had tried to use them in the treatment of allergic or eosinophilic diseases, in which IL-5 is thought to play an important role.

As shown in the examples below, the inventors found that nonactin inhibits human IL-5 production by human T-cells and that this inhibitory effect is due to the inhibition of protein production by inhibition of human IL-5 gene transcription and mRNA expression.

Figure 1:
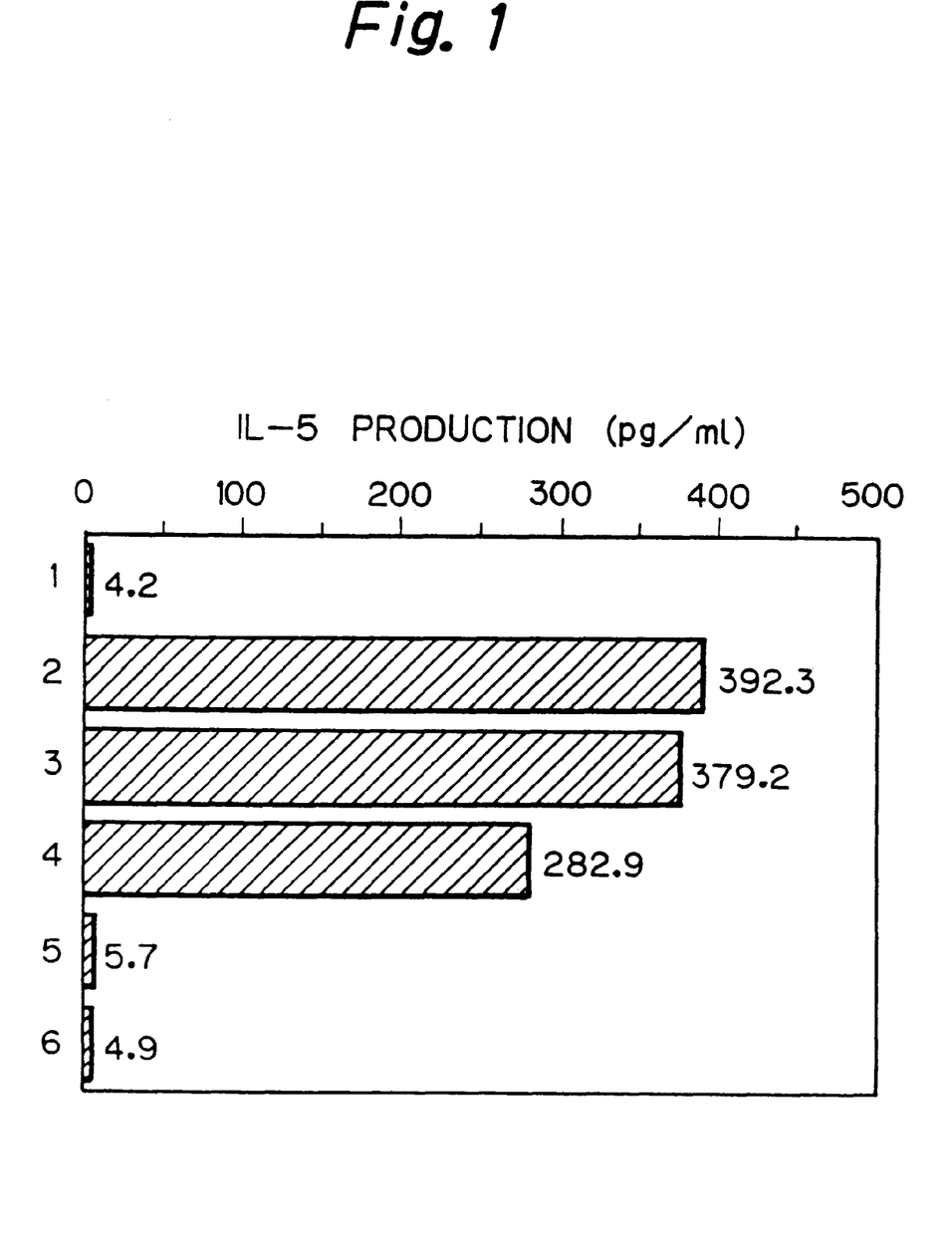
FIG. 1 shows the inhibition by nonactin of IL-5 production by peripheral mononuclear cells obtained from allergic patients. The numbers in this figure indicate the following.
Figure 2:
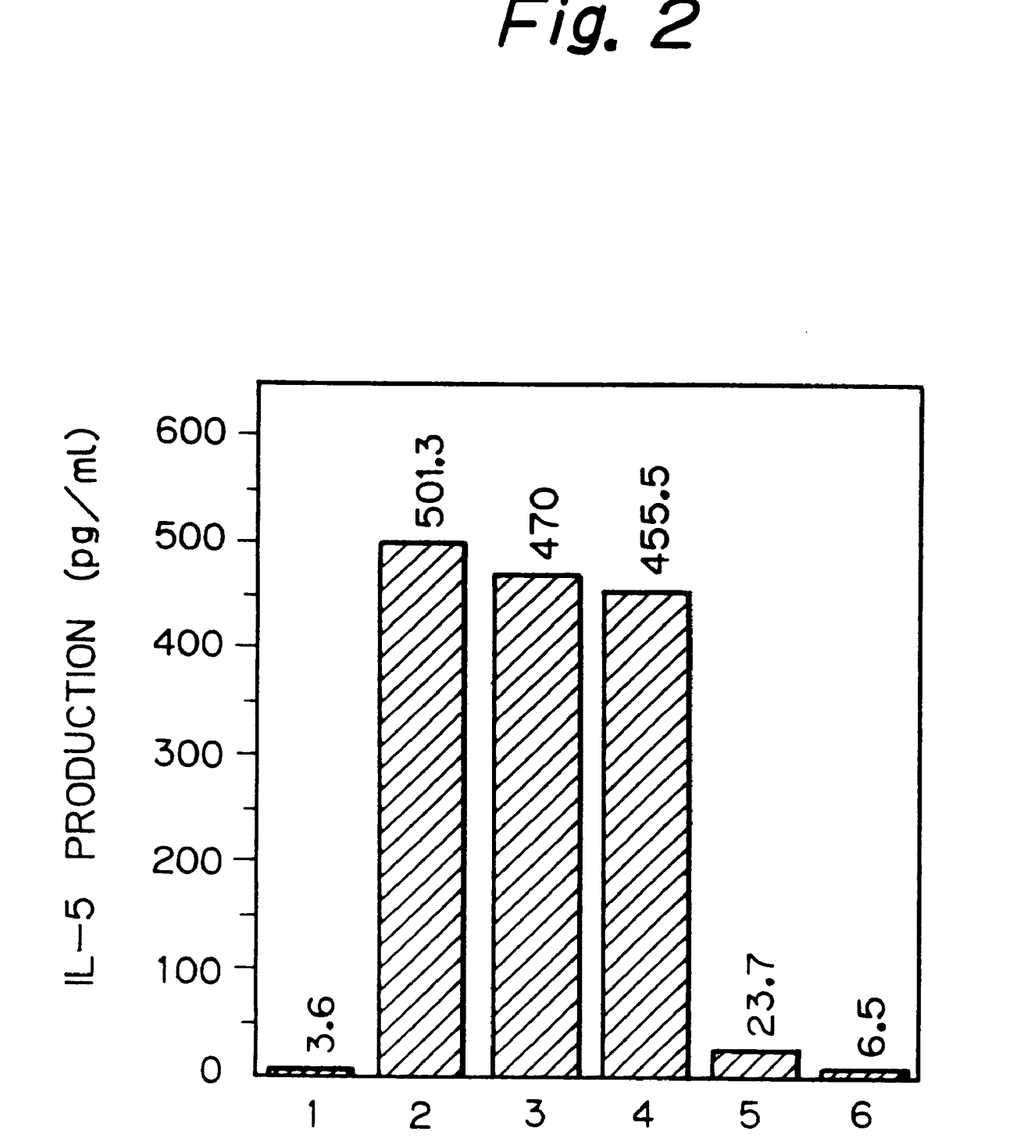
FIG. 2 shows the inhibition by nonactin of IL-5 production by T-cell clones. The numbers in this figure indicate the following.

Nonactin dose-dependently inhibited the production of IL-5 when it was added to cultured mononuclear cells from peripheral blood of allergic patients under stimulation by concanavalin A, which activates T-cells via their antigen receptors (FIG. 1). The inventors demonstrated that when peripheral blood mononuclear cells were stimulated with concanavalin A, IL-5 was almost exclusively produced from CD4+T-cells, so nonactin is thought to inhibit IL-5 production from these cells. In order to demonstrate that nonactin directly affects T-cells, the authors established allergen-specific T-cell clones and added nonactin to T-cell clones which have the ability to produce large amounts of IL-5 using solid-phased anti-CD3 monoclonal antibody, a T-cell receptor-mediated stimulator. Nonactin completely inhibited IL-5 production at 100 nM and higher concentrations (FIG. 2).

Figure 3:
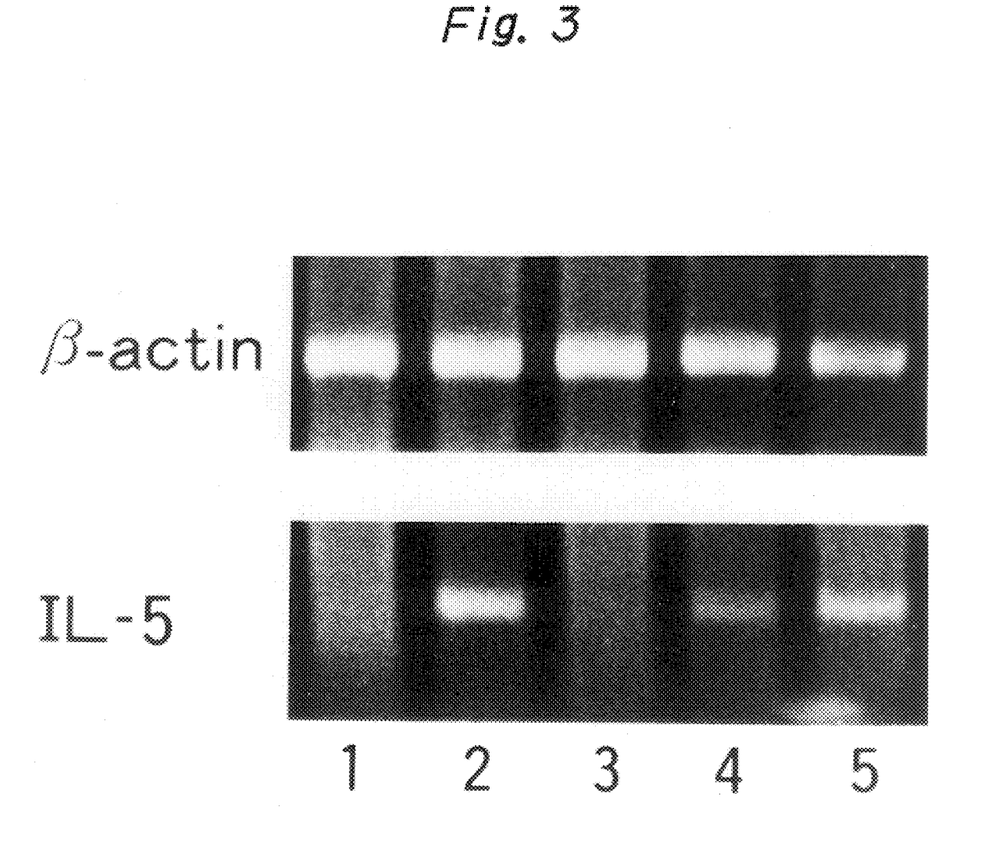
FIG. 3 shows electrophoretograms which indicate the inhibition by nonactin of IL-5 gene transcription in peripheral mononuclear cells from allergic patients. The lane numbers in this figure show the following.
Figure 4:
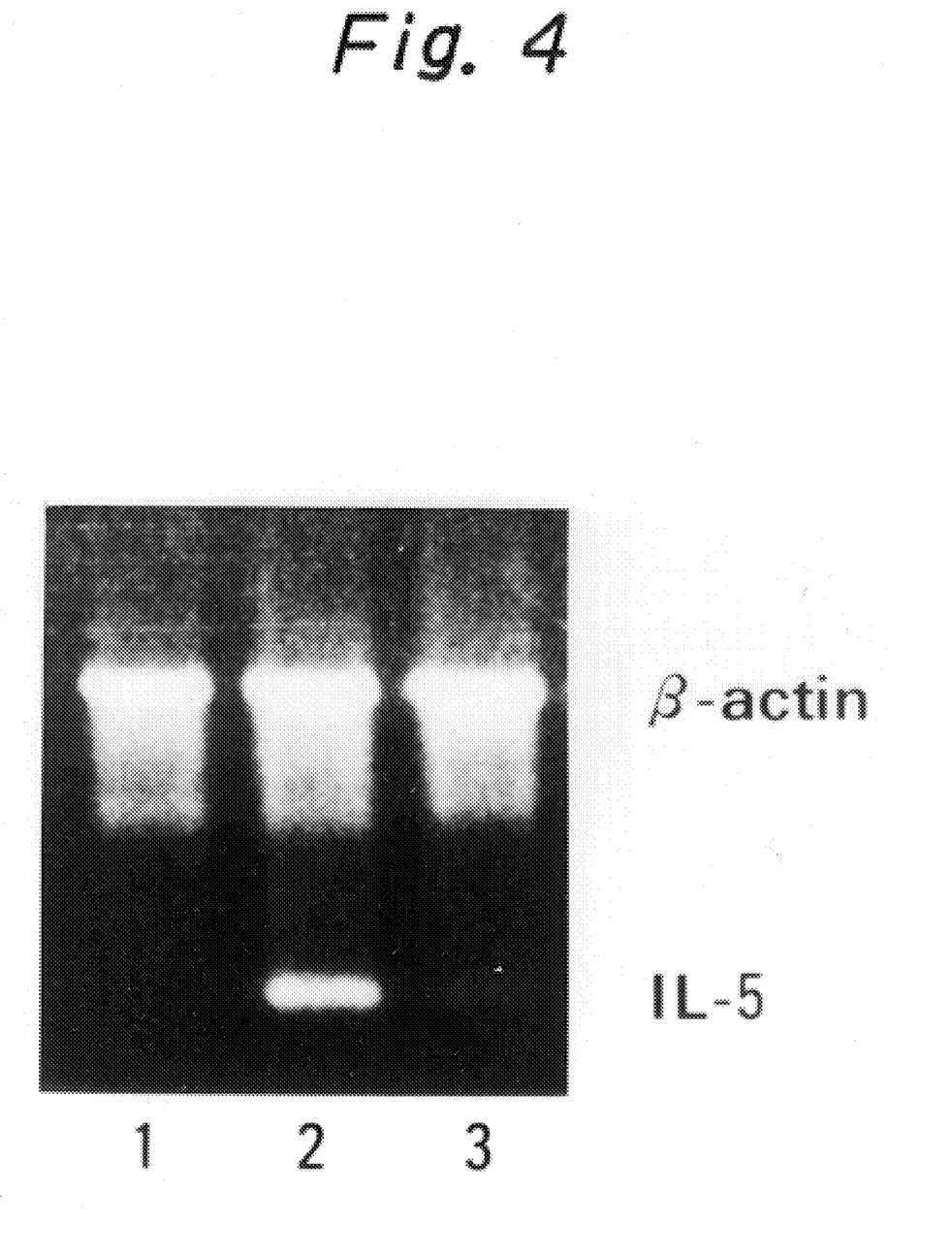
FIG. 4 shows electrophoretograms which indicate the inhibition by nonactin of IL-5 gene transcription in T-cell clones. The figures in these pictures indicate the following.

The inventors conducted another experiment similar to that shown in FIG. 1 in order to determine whether the inhibition by nonactin of IL-5 production is mediated by the inhibition of IL-5 gene expression (mRNA expression), and demonstrated that nonactin dose-dependently inhibits IL-5 gene expression by the RT-PCR (reverse transcription-polymerase chain reaction) method (FIG. 3). The fact that nonactin directly affects T-cells and inhibits IL-5 mRNA expression was demonstrated by the fact that it inhibits IL-5 mRNA expression induced by T-cell clones stimulated by phorbol ester and $Ca^{++}$ ionophore (FIG. 4). When T-cells are activated by physiologically active antigens in vivo, intracellular protein kinase C (PKC) is activated by T-cell receptor-mediated active signals, resulting in $Ca^{++}$ influx. Stimulation by phorbol ester (PMA), which directly activates PKC, and $Ca^{++}$ ionophore (ionomycin: IOM), which causes $Ca^{++}$ influx, is commonly used in immunological experiments, because it results in activation comparable to that achieved by the stimulation of T-cells by antigens.

In order to evaluate the effects of nonactin on IL-5 gene transcription, the investigators prepared human IL-5 gene expressing T-cell hybridomas by fusing the above-mentioned T-cell clones with human T-cell tumor cell lines. Nonactin's inhibitory effects on gene transcription were tested in a gene transcription experimentation system obtained by transiently transfecting to these T-cell hybridomas with pIL-5 Luc (FIG. 6) obtained by connecting the DNA in the promoter/enhancer region 5' upstream the origin of human IL-5 gene transcription to luciferase genes (reporter genes). When pIL-5 Luc is transiently introduced into cells of IL-5 gene expressing T-cell hybridomas and stimulated by PMA+IOM, the IL-5 gene transcription apparatus (transcription factor) induced in cells recognizes and combines IL-5 promoter/enhancer regions and transcribes luciferase genes located downstream, leading to the appearance of luciferase mRNA in cells and rapid production of luciferase protein. Unlike cytokine's mRNA, luciferase's mRNA is very stable, and protein is synthesized from mRNA at a constant rate, making it possible to determine whether nonactin affects IL-5 gene promoters/enhancers. In this experimental system, nonactin was found to inhibit the expression of functions of human IL-5 gene promoters/enhancers at 100 nM and 1 μM, thereby inhibiting the transcription of IL-5 genes (FIG. 7).

Like steroids and the immunosuppressive agents FK506 and cyclosporine A, therefore, nonactin and its related substances are useful as therapeutic agents for allergic and eosinophilic diseases.

Figure 8:
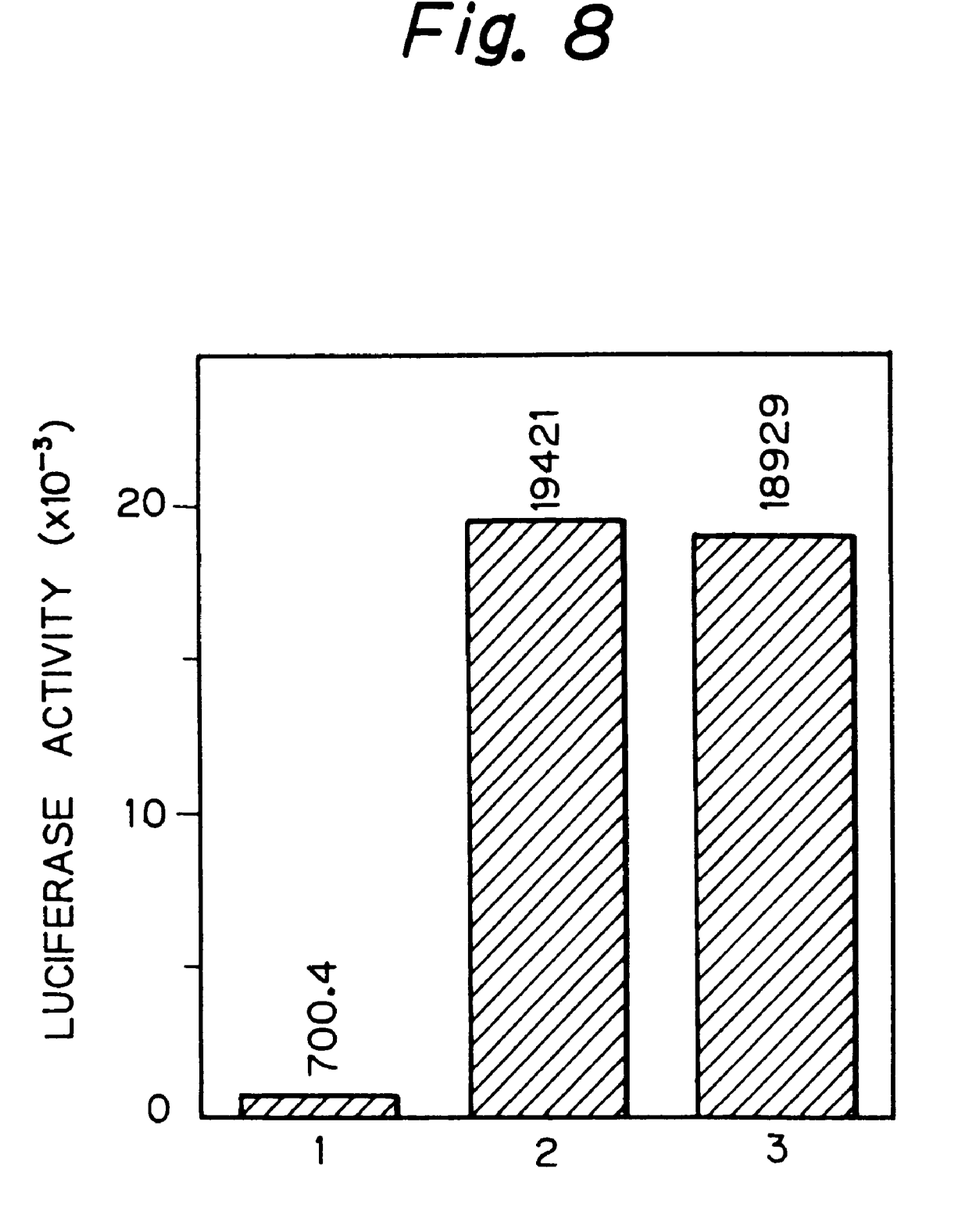
FIG. 8 shows the effects of nonactin on IL-2 gene transcription determined by measuring pIL2 Luc-derived luciferase activity. The figures in this figure indicate the following.
Figure 9:
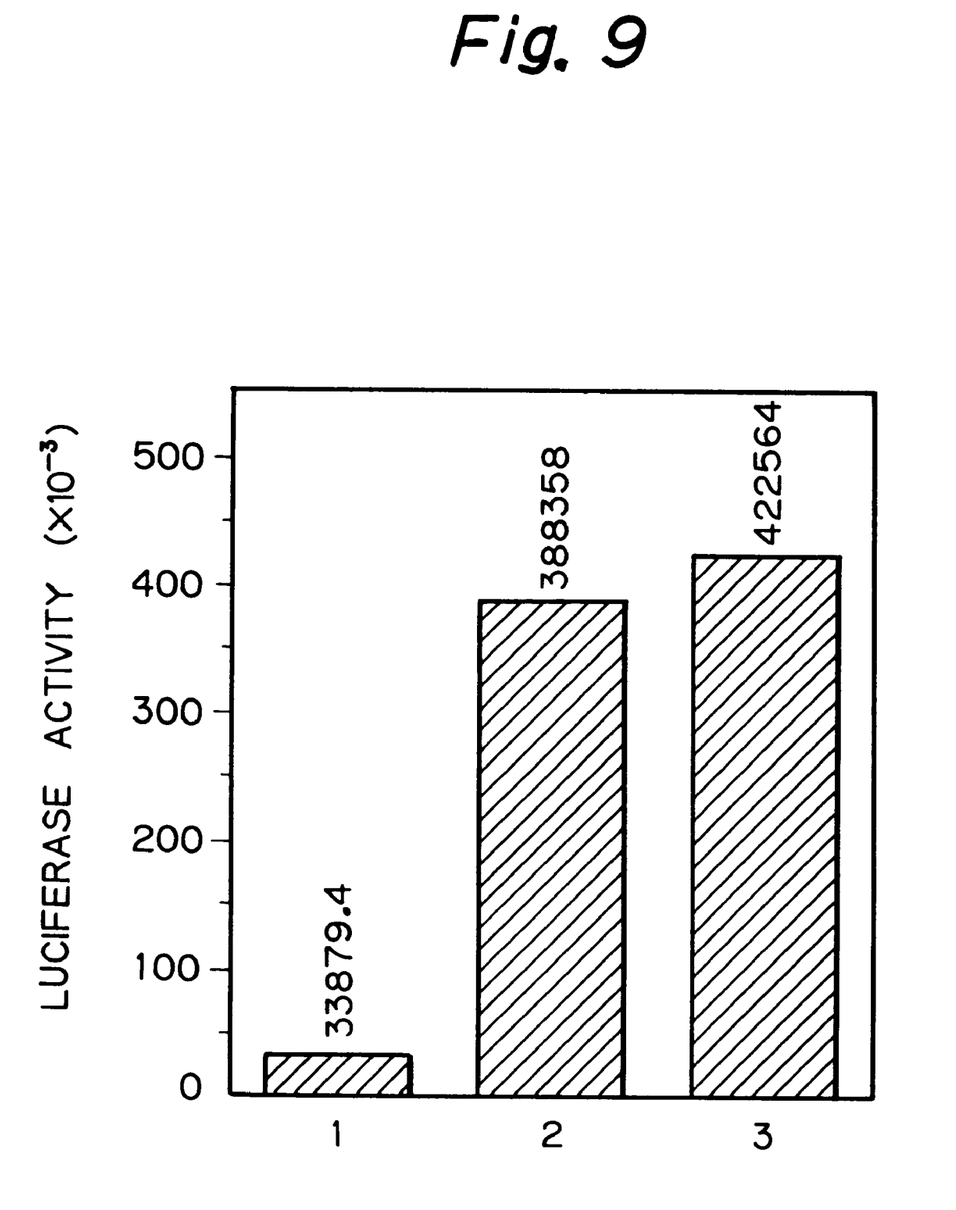
FIG. 9 shows the effects of nonactin on IL-4 gene transcription determined by measuring pIL4 Luc-derived luciferase activity. The figures in this figure indicate the following.

In similar experiments, nonactin inhibited the production of neither IL-2 nor IL-4 (FIG. 5) nor their gene transcription (FIGS. 8 and 9). This finding suggests that the compounds used in the present invention have little effect on other immune systems, such as anti-infection immunity, and therefore make it possible to avoid adverse effects of cyclosporine and FK-506, such as increased susceptibility to infections and development of malignant tumors due to impaired immunity. They are also expected to be free of the various adverse effects of steroids mentioned above, making them promising, safe drugs for allergic and eosinophilic drugs.

Furthermore, nonactin blocked the recruitment of eosinophils in an in vivo study conducted using BDF1 mice sensitized with ovalbumin (FIG. 10), suggesting that compounds used in the present invention inhibit eosinophilic inflammation in vivo and that they are useful for the treatment of allergic and eosinophilic diseases.

According to the present invention, formula I compounds can be administered alone or in combination for the treatment of allergic or eosinophilic diseases. These compounds may be administered either per se or in the form of granules, tablets, hard or soft capsules, granules, powder, fine granules, emulsions, oral liquid or any other dosage forms manufactured using solid or fluid carriers for pharmaceutical use for oral, intravenous, intramuscular, intradermal or subcutaneous administration. Parenteral dosage forms may be prepared using powder before use. These compounds may also be administered locally into the rectum, nose, eyes and lungs in the form of suppositories, nasal or eye drops and inhalation drugs. Inhalation drugs may be aqueous or partially aqueous solutions for administration in aerosol form.

The ratio of compounds shown by formula I to carriers may vary between 0.01 and 90 w/w % in the case of solid dosage forms. Appropriate carriers for solid dosage forms include lactose, dextrin, starch, calcium carbonate, etc. These dosage forms can be prepared using the conventional method.

In the case of fluid dosage forms, such as emulsions, suspensions, syrup and oral liquid, water, alcohol and its derivatives, and oils (fractionated coconut oil, peanut oil, etc.) can be used as carriers. In case of parenteral administration, oily esters such as oleic acid ethyl and myristic acid isopropyl can be used as carriers. These dosage forms can be prepared using the conventional method.

Compounds shown by formula I can also be added to permitted diluents in amounts necessary to obtain clinical efficacy and can be administered locally as liquid, ointment, cream and lotion.

Doses can be titrated according to the compounds used, administration route, severity of symptoms and patients' characteristics. In general, desirable doses range between 0.1 and 100 mg/kg/day. Safe clinical doses must be determined in clinical safety studies in the future (Phase I). Optimal doses and blood concentrations will be determined in therapeutic concentration determination studies (Phase II).

The present invention is explained in more detail below with reference to examples, but it is by no means limited to these examples.

EXAMPLE 1

Inhibition By Nonactin Of IL5 Production

1) Inhibition of IL-5 production by peripheral blood mononuclear cells from allergic patients The inventors already reported that IL-5 production by peripheral T-cells is increased in allergic patients (Mori A. et al, International Immunology 7: in press). In that study, the inventors collected venous blood samples from some patients with increased IL-5 production with their consent.

Peripheral blood mononuclear cells (PBMC) were separated from collected blood samples by Ficoll-Paque specific gravity centrifugation, suspended in AIM-V medium at $2 \times 10^6$ cells/well and cultured using a 24-well plate (Corning). Nonactin (Sigma) was added after stimulation with 10 $\mu$g/ml of concanavalin A (Con A). The supernatant was collected after culturing for 48 hours, and IL-5 was determined using a specific ELISA method. Results obtained are shown in FIG. 1. As shown in this figure, nonactin dose-dependently inhibited IL-5 production.

2) Inhibition of IL-5 production by allergen-specific T-cell clones

Peripheral blood mononuclear cells from allergic patients were stimulated by Der f II protein, a major allergen contained in house dust, and T-cell clones were established by the limiting dilution method (Mori A. et al, International Archives of Allergy and Immunology, 1995 in press). Clones ($10^5$ cells/well) which produce IL-5 upon stimulation by the antigen were incubated in a 96-well round-bottom culture plate. Production of IL-5 by T-cell clones was observed upon CD3 molecule-mediated stimulation in wells pre-coated with 10 $\mu$g/ml of anti-CD3 monoclonal antibodies (OKT3: Janssen Kyowa). Nonactin completely inhibited IL-5 production at 100 nM or higher concentrations (FIG. 2).

EXAMPLE 2

Inhibition By Nonactin Of IL5 Gene Expression

1) Inhibition of IL-5 mRNA expression by PBMC from allergic patients

Effects of nonactin on IL-5 mRNA expression were investigated by the reverse transcription-polymerase chain reaction (RT-PCR) method (Mori A. et al, International Immunology: 7, 449–457).

PBMC separated from peripheral blood of allergic patients as motioned above were cultured at $2 \times 10^6$ cells/well using a 24-well plate (Corning) and stimulated using 10 $\mu$g/ml of Con A. Nonactin was added upon start of culture. Cells were harvested 8 hours later and 1 ml of Isogen (Nippon Genes) was added to pellets in order to dissolve cells. Cells were then homogenized 10 times using a 5 ml-syringe with a 25G needle and centrifuged at 13,000 rpm for 15 min at 4° C. after addition of 200 $\mu$l of chloroform and thorough mixing. The aqueous layer was collected and 500 $\mu$l of isopropyl alcohol was added. After stirring, the mixture was cooled for at least 1 hour at –20° and centrifuged at 13,000 rpm for 15 min at 4° C. After decantation, 80% ethanol was added to pellets to wash and the pellets were centrifuged at 13,000 rpm for 15 min at 4° C. After decantation, 400 $\mu$l of TE buffer (10 mM Tris-HCl, pH 8.0, 5 mM EDTA), 40 $\mu$l of 3M sodium acetate solution (pH 5.3) and 1 ml of 100% ethanol were added to pellets and the pellets were cooled for at least 1 hour at –20° C. After centrifugation at 13,000 rpm for 15 min at 4° C. and decantation, the pellets were dried at room temperature and dissolved in 10 $\mu$l of distilled water. After incubation for 4 min at 70° C., the solution obtained was rapidly cooled on ice. 9.5 $\mu$l of the RT reaction fluid shown in Table 1 below was added and the mixture obtained was allowed to react for 3 hours at 42° C. to synthesize cDNA (reverse transcription: RT).

TABLE 1

| 5× First buffer: | 4 $\mu$l |
| 0.1M DTT: | 1 $\mu$l |
| RNasin 40 U/$\mu$l: | 1 $\mu$l |
| dNTPmix (10 mM): | 1 $\mu$l |
| random primer: | 1.5 $\mu$l |
| Reverse transcriptase: | 1 $\mu$l |

After completion of reaction, the PCR reaction fluid shown in Table 2 was prepared and 45 $\mu$l was added to 5 $\mu$l of cDNA.

TABLE 2

| 10× PCR reaction Buffer: | 5 $\mu$l |
| 2.5 mM MgC12: | 3 $\mu$l |
| Sterile water: | 32.6 $\mu$l |
| dNTpmix (10 mM): | 2 $\mu$l |
| 20 $\mu$M 5'-I L-5 primer: | 1 $\mu$l |
| 20 $\mu$M 3'-I L-5 primer: | 1 $\mu$l |
| 20 $\mu$M 5'-β Bactin primer: | 1 $\mu$l |
| 20 $\mu$M 3'-β Bactin primer: | 1 $\mu$l |
| Taq polymerase 5 U/$\mu$l: | 0.4 $\mu$l |

In addition, 33 $\mu$l of light mineral oil was added and the PCR method was conducted according to the protocol shown in Table 3.

TABLE 3

| Step 1 | |
| --- | --- |
| 2:30 | 95° C. |
| 1:30 | 72° C. |
| 2:00 | 60° C. |
| Step 2–30 cycle repeat | |
| 1:00 | 95° C. |
| 1:30 | 72° C. |
| 2:00 | 60° C. |

After completion of PCR, 2 μl of 6x Type III dye (Nippon Genes) was added to 10 μl of each sample and electrophoresis was carried out using 0.5×TBE 1% agarose gel.

Beta-actin was used as the positive control.

Nonactin significantly inhibited IL-5 mRNA expression at 100 nM or higher concentrations (FIG. 3).

2) Inhibition of IL-5 mRNA by allergen-specific T-cell clones

The Der f II-specific T-cell clones described in Section 2) of Example 1 were stimulated by 20 nM phorbol 12-myristate 13-acetate (PMA) and 1 μM ionomycin (IOM) and cells were harvested 6 hours later. Nonactin was added upon start of incubation. RNA was extracted as mentioned in 2) above and IL-5 mRNA expression was determined by the RT-PCR method. As shown in FIG. 4, nonactin showed no effect on actin gene expression but effectively inhibited IL-5 mRNA expression.

EXAMPLE 3

Effects Of Nonactin On IL-2 And IL-4 Expression

Figure 5A:
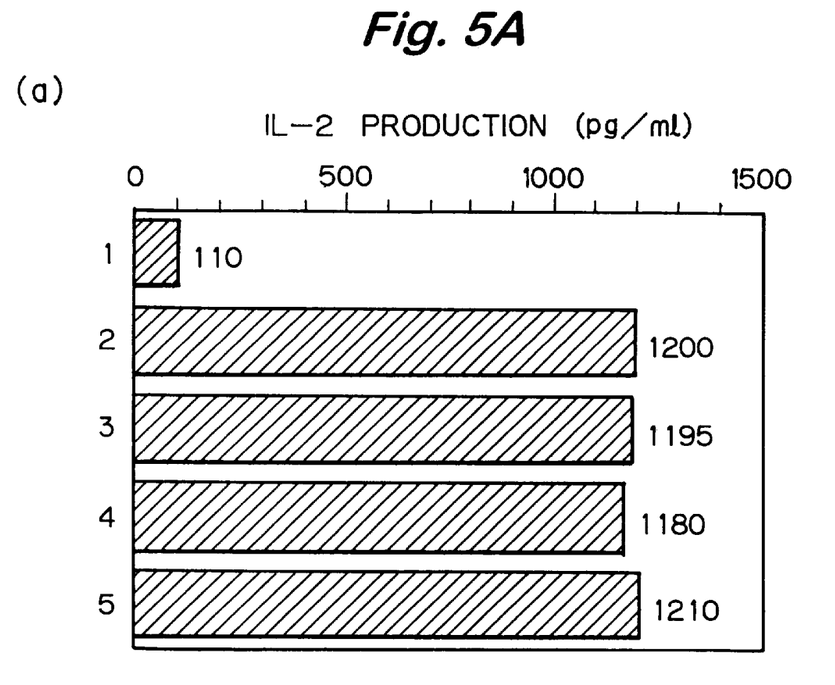
Figure 5B:
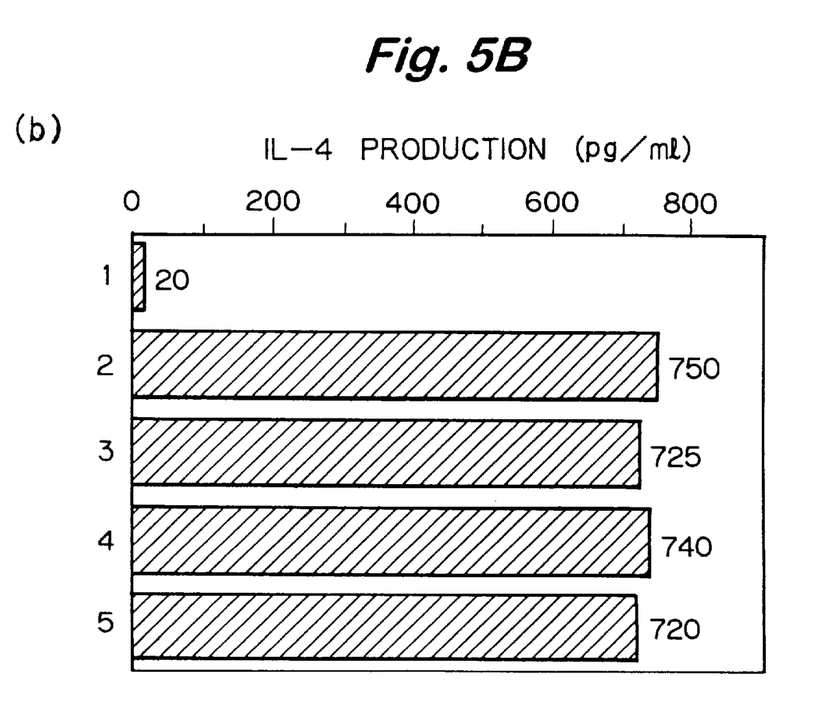

PBMC was separated from peripheral blood of allergic patients as mentioned in Example 1, incubated in a 24-well plate at 2×10$^6$ cells/well and stimulated with 10 μg/ml of Con A. Nonactin was added at the same time. After incubation for 48 hours, the supernatant was collected and determination was carried out using IL-2 and IL-4 ELISA kits (R&D System). Nonactin did not inhibit the production of IL-2 and IL-4 between 100 nM and 1 μM (FIG. 5).

EXAMPLE 4

Inhibition By Nonactin Of Human Cytokine Gene Transcription

1) Effects on IL-5 gene transcription

Figure 6A:
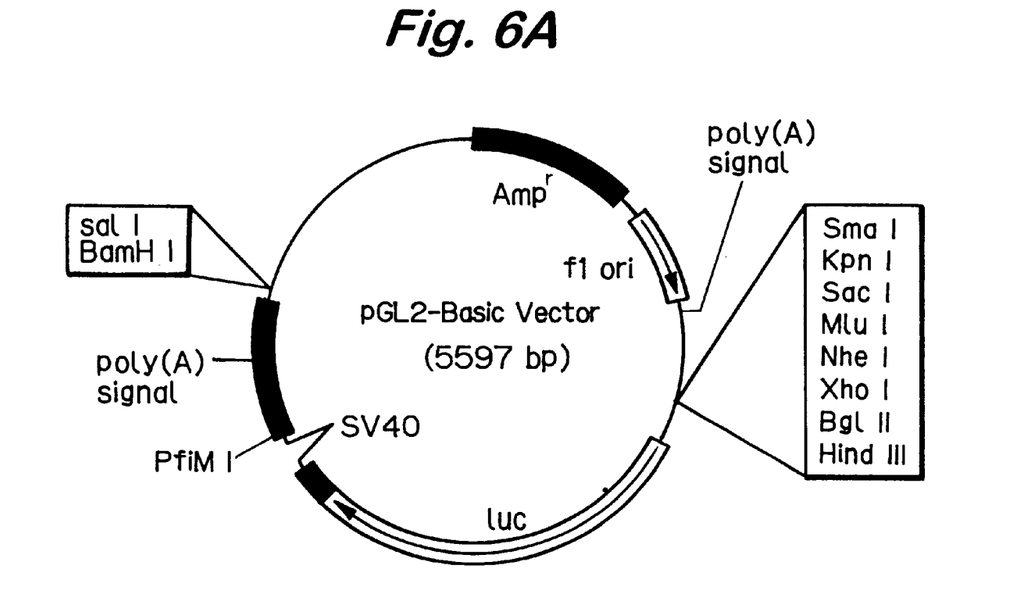
FIG. 6 shows the simulated structure of plasmid pIL5 Luc.
Figure 6B:
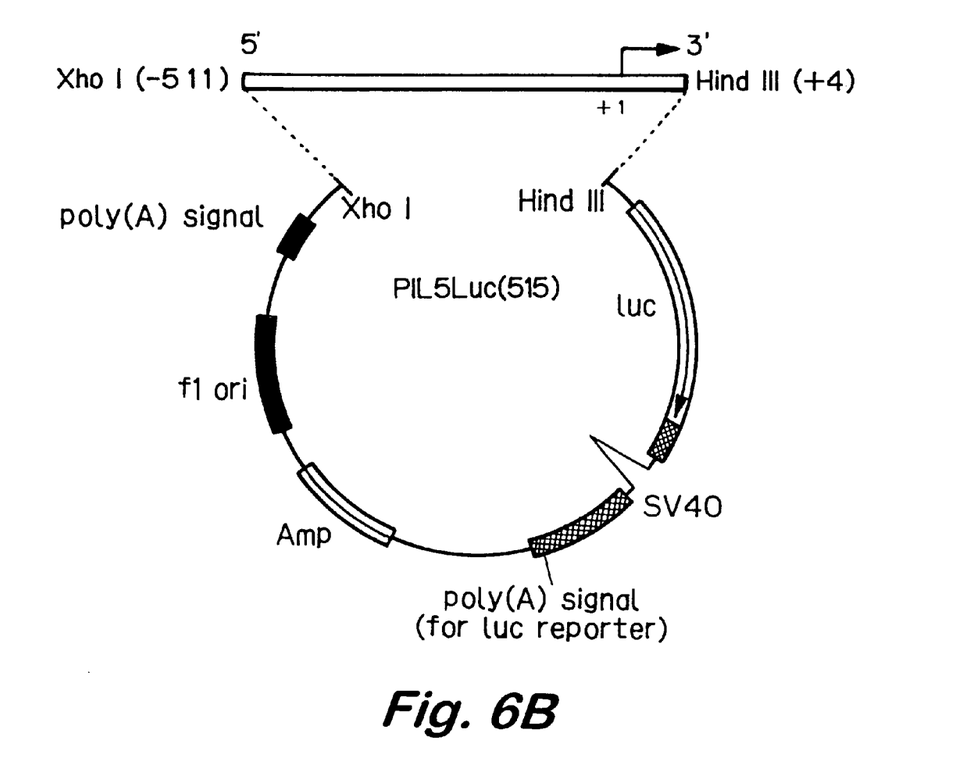
Figure 7:
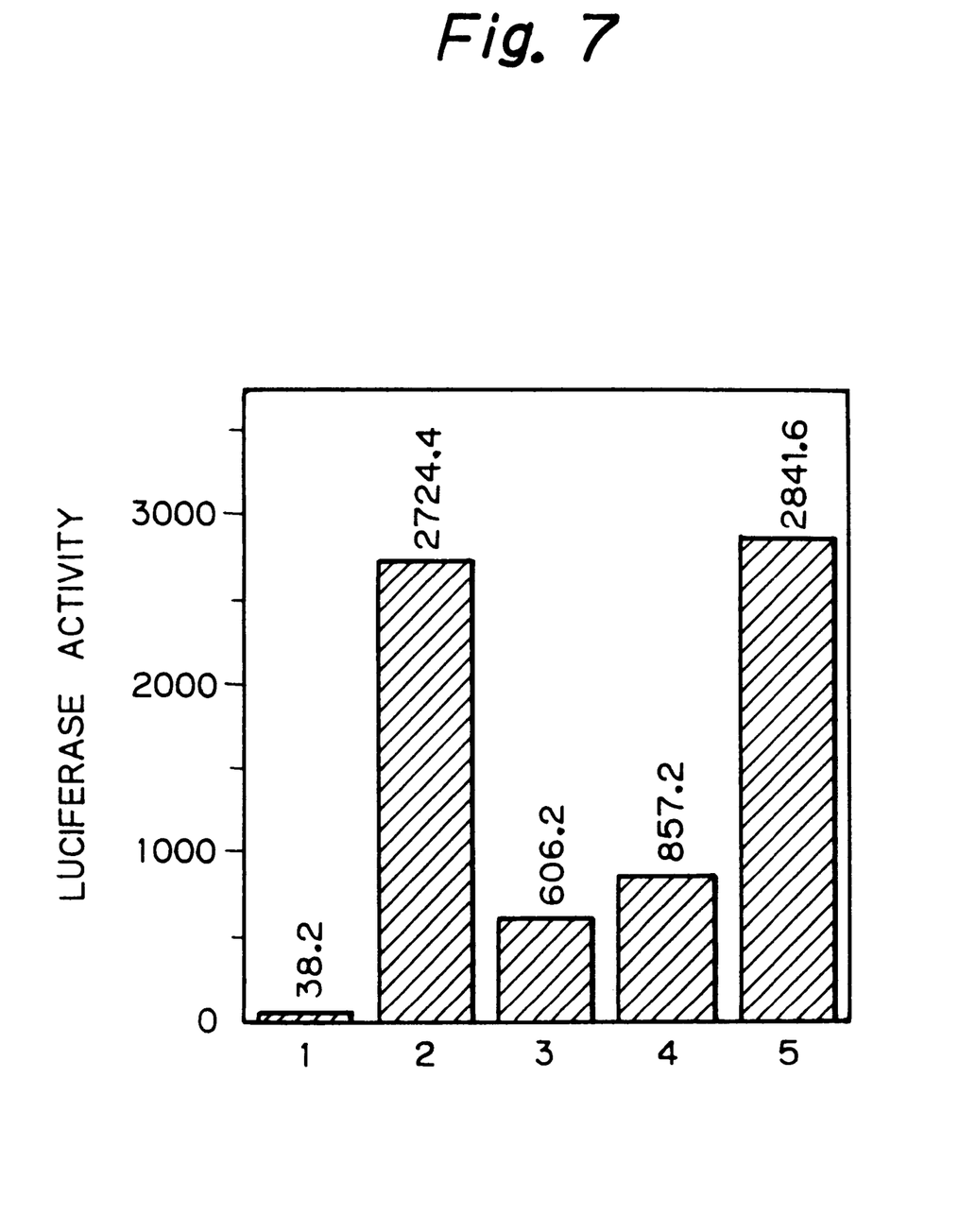
FIG. 7 shows the effects of nonactin on IL-5 gene transcription determined by measuring pIL5 Luc-derived luciferase activity. The numbers in this figure indicate the following.

Human IL-5 gene expression T-cell hybridomas were obtained by fusing the T-cell clones mentioned above with a human T-cell tumor cell line (Mori A. et al, International Archives of Allergy and Immunology, 1995 in press).

pIL-5 Luc was prepared by connecting DNA of about 500 bp in the human IL-5 gene promoter/enhancer region to luciferase genes (reporter genes) (FIG. 6). T-cell hybridomas (5×10$^6$) were suspended in 0.5 ml of RPMI medium (Gibco BRL) and 10 μg of pIL-5 Luc was transiently transfected by the electropolation method at 250V and 800 μF. After washing, cells were stimulated by 20 nM of PMA and 1 μM of IOM and cells were harvested 24 hours later. Induced luciferase activity was determined using a luciferase assay system (Toyo Ink Mfg. Co., Ltd.). As shown in FIG. 7, nonactin completely inhibited pIL-5 Luc-derived luciferase activity at 100 nM and 1 μM, indicating that it inhibits IL-5 gene transcription by inhibiting the expression of human IL-5 gene promoter/enhancer functions.

2) Effects on IL-2 gene transcription

The vector pIL-2 Luc was prepared as mentioned in 1) above by connecting DNA of 275 bp in the human IL-2 gene promoter/enhancer region to luciferase genes. Ten μg of pIL-2 Luc was transfected to the above-mentioned human T-cell hybridomas using the electropolation method and stimulated for 48 hours with PMA and IOM. Induced luciferase activity was determined. As shown in FIG. 8, nonactin did not inhibit IL-2 gene transcription at 100 nM.

3) Effects on IL-4 gene transcription

The vector pIL-4 Luc was prepared by connecting DNA of 270 bp in the human IL-4 gene promoter/enhancer region to luciferase genes. Ten μg of pIL-4 Luc was transfected to the human T-cell hybridomas and stimulated for 48 hours with PMA and IOM. As shown in FIG. 9, nonactin did not inhibit IL-4 gene transcription at 100 nM.

Experiments described in 1), 2) and 3) above showed that nonactin is induced as allergen-specific human T-cell hybridomas are activated and has no effect on IL-2 or IL-4 gene transcription but effectively inhibits IL-5 gene transcription.

EXAMPLE 5

Inhibition By Nonactin Of Eosinophil Infiltration In Vivo (a) Six-week-old BDF1 mice were sensitized by administering 1 μg of ovalbumin (OA) and 1 mg of aluminum hydroxide gel (Alum) twice at 2-week intervals. Two weeks later, nonactin and the vehicle control (saline) were subcutaneously administered for 3 consecutive days at 2 mg/animal (100 mg/kg). Thirty minutes after administration of nonactin or the vehicle on the 3rd day, the antigen (100 mg/mil of ovalbumin in saline) was administered by inhalation for 10 min.

Twenty-four hours later, the cells were harvested by bronchoalveolar lavage and total cells were counted. Cell fractions were stained and analyzed using cell-staining techniques.

Figure 10A:
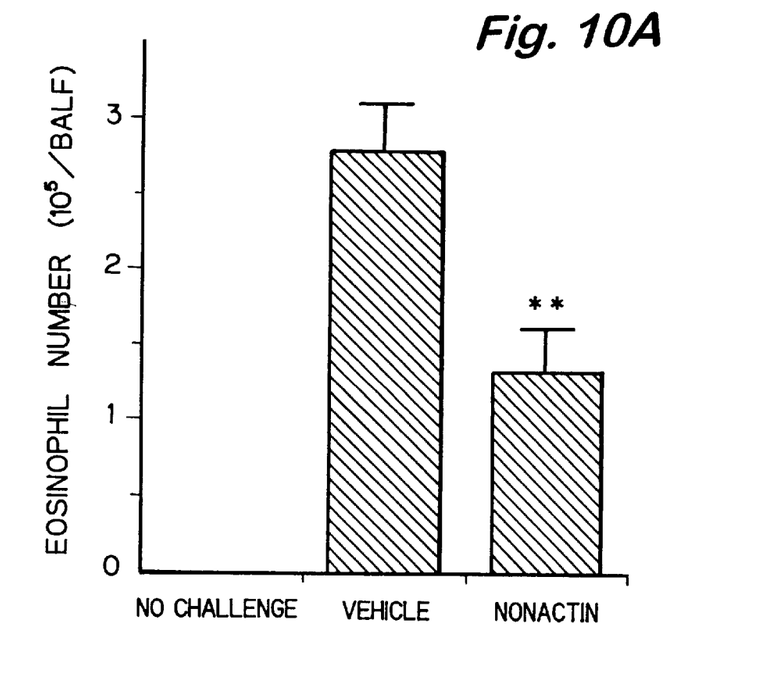
FIG. 10a shows in vivo inhibitory effects on eosinophil infiltration of nonactin administered for 3 days after sensitization at 100 mg/kg. The figures in this figure indicate the following.

As shown in FIG. 10*a*, nonactin inhibited eosinophil infiltration by blocking IL-5-dependent eosinophil recruitment in vivo.

(b) Six-week-old BDF1 mice were sensitized by administering 1 μg of ovalbumin (OA) and 1 mg of aluminum hydroxide gel (Alum) twice at 2-week intervals. Eight days later (day 22), nonactin and the vehicle control (saline) were subcutaneously administered for 7 consecutive days at 60 μg/animal (3 mg/kg). Thirty minutes after administration of nonactin or the vehicle on the 7th day (day 28), the antigen (100 mg/ml of ovalbumin in saline) was administered by inhalation for 10 min.

Twenty-four hours later, cells were harvested by bronchoalveolar lavage and total cells were counted. Cell fractions were stained and analyzed using cell-staining techniques.

Figure 10B:
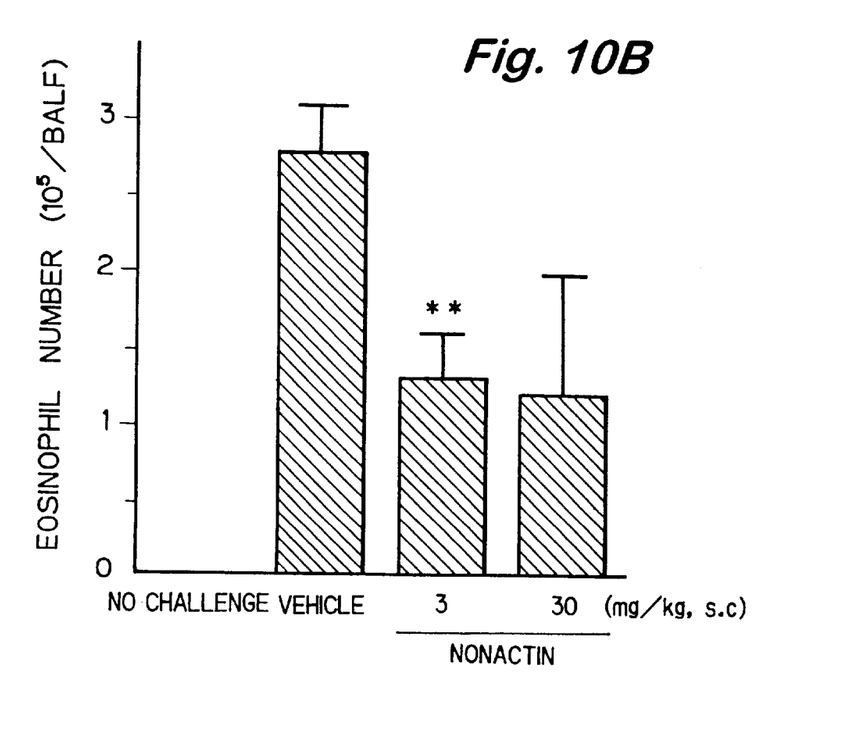
FIG. 10b shows in vivo inhibitory effects on eosinophil infiltration of nonactin administered once daily for 7 days after sensitization at 3 mg/kg.

As shown in FIG. 10*b*, nonactin clearly inhibited eosinophil infiltration by blocking IL-5-dependent eosinophil recruitment in vivo even at a very low dose (3 mg/kg).

What is claimed is:

1. A method of treating an allergic disease selected from the group consisting of bronchial asthma, atopic dermatitis, pollinosis, allergic rhinitis and allergic conjunctivitis, which comprises administering to a patient having said disease a therapeutically effective amount of one or more compounds selected from those shown by formula I below in which $R_1$, $R_2$, $R_3$ and $R_4$ are each independently a $C_1$–$C_6$ alkyl group 2. A method of treating an eosinophilic inflammatory disease selected from the group consisting of eosinophilic syndrome, allergic angiitis, eosinophilic fasciitis, eosinophilic pneumonitis and PIE syndrome, comprising administering to a patient having said disease a therapeutically amount of one or more compounds selected from those shown by formula I below in which $R_1$, $R_2$, $R_3$ and $R_4$ are each independently a $C_1$–$C_6$ alkyl group 3. A method of treatment according to claim 2, in which the compounds shown by formula I are selected from the group consisting of nonactin, monactin, dinactin, tetranactin and trinactin.

4. A method of treatment according to claim 1, in which the compounds shown by formula I are selected from the group consisting of nonactin, monactin, dinactin, tetranactin and trinactin.

* * * * *

UNITED STATES PATENT AND TRADEMARK OFFICE
CERTIFICATE OF CORRECTION

PATENT NO. : 5,962,511
DATED : October 5, 1999
INVENTOR(S) : Itirokazu OKUDAIRA et al.

It is certified that error appears in the above-identified patent and that said Letters Patent is hereby corrected as shown below:

ON THE FACE OF THE PATENT

[62]   Related U.S. Application Data

After "Division of application No. 08/841,683, Apr. 30, 1997, abandoned" please add:

--, which is a continuation of application No. 08/527,188, Sep. 12, 1995, Pat. No. 5,721,270--

Signed and Sealed this

Tenth Day of April, 2001

*Attest:*

NICHOLAS P. GODICI

*Attesting Officer*   *Acting Director of the United States Patent and Trademark Office*